(12) United States Patent
Verma (10) Patent No.: US 8,256,243 B2
(45) Date of Patent: Sep. 4, 2012

(54) INTEGRATED OLEFIN RECOVERY PROCESS

(75) Inventor: Vijender Kumar Verma, Sugar Land, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 1564 days.

(21) Appl. No.: 11/639,907

(22) Filed: Dec. 16, 2006

(65) Prior Publication Data

US 2008/0141712 A1 Jun. 19, 2008

(51) Int. Cl.
*F25J 3/00* (2006.01)

(52) U.S. Cl. ............ 62/620; 62/617; 62/618; 62/619; 62/630; 62/631

(58) Field of Classification Search ............ 62/617, 62/618, 619, 620, 630, 631
See application file for complete search history.

(56) References Cited

U.S. PATENT DOCUMENTS

| 4,452,281 | A | | 6/1984 | Speich | |
|---|---|---|---|---|---|
| 4,885,063 | A | * | 12/1989 | Andre | ............ 203/73 |
| 4,900,347 | A | | 2/1990 | McCue, Jr. et al. | |
| 5,421,167 | A | | 6/1995 | Verma | |
| 5,453,559 | A | | 9/1995 | Phillips et al. | |
| 5,884,504 | A | * | 3/1999 | Nazar | ............ 62/630 |
| 6,021,647 | A | | 2/2000 | Ameringer et al. | |
| 6,077,985 | A | * | 6/2000 | Stork | ............ 585/800 |
| 6,405,561 | B1 | | 6/2002 | Mortko et al. | |
| 6,516,631 | B1 | | 2/2003 | Trebble | |
| 6,601,406 | B1 | | 8/2003 | Deng et al. | |
| 2005/0229634 | A1 | * | 10/2005 | Huebel et al. | ............ 62/632 |

* cited by examiner

*Primary Examiner* — Frantz Jules
*Assistant Examiner* — Azim Abdur Rahim
(74) *Attorney, Agent, or Firm* — KBR IP Legal Dept.

(57) ABSTRACT

Methods and apparatus for the integration of a fractionation process and an olefin refrigeration system, wherein the fractionation process olefin effluent is supplied to the refrigeration system, can eliminate a fractionation process condenser and reflux drum typically present. A plurality of bottoms streams can be collected from the fractionation process. The olefin refrigerant can be supplied to alternate olefin refrigerant consumers, as desired. A column in the fractionation process can be refluxed with an olefin stream from refrigeration system, and olefin product can be collected or exported via line.

8 Claims, 11 Drawing Sheets

INTEGRATED OLEFIN RECOVERY PROCESS

FIELD

The embodiments relate to improved olefin recovery processes, such as olefin recovery processes integrating a fractionation column and an olefin refrigeration system to reduce the number of pieces of equipment necessary for the olefin recovery process, thereby reducing the overall costs associated with the construction of a recovery plant.

BACKGROUND

Olefins can be recovered from a hydrocarbon stream produced from catalytic reactors and/or thermal cracking furnaces that are well known in the art, including for example, Superflex™ deep catalytic cracking processes and fluid catalytic cracking (FCC) reactors. The feed gas to the recovery process from the reactor/furnace effluent, typically comprises olefins and alkanes and must be processed to separate and recover the various different fractions from the feed stream, which can include hydrogen, methane, ethane, ethylene, propane, propylene, butane, butylenes, and heavier hydrocarbons. Various methods for the separation of the feed stream into the respective component fractions is well known in the art, and generally involve a combination of absorption, adsorption chilling, expansion, fractionation and/or like operations.

In separation processes, conventional deethanizers can be used to separate the C2 and C3 components to produce separate C2 and C3 fractions. The C2 and C3 fractions can then be further treated in C2 and C3 splitters respectively, to produce nearly pure ethylene and ethane, and nearly pure propylene and propane respectively. The bottoms streams from the splitters can be recycled to the pyrolysis furnace for further cracking or produced as a product.

Figure 2:
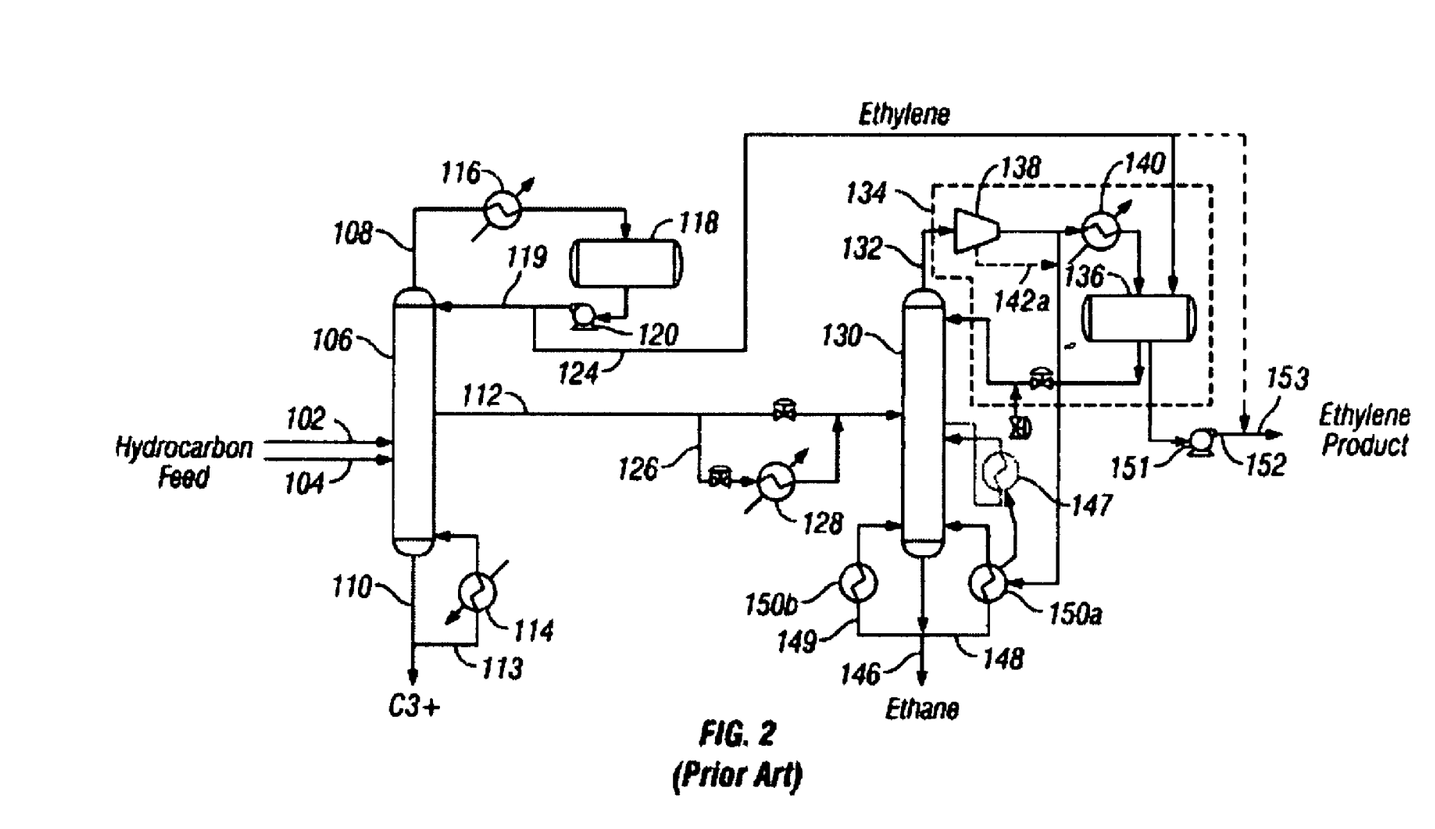
FIG. 2 is a schematic illustration of a prior art ethylene/ethane separation unit featuring an advanced deethanizer, an ethylene/ethane splitter, and an ethylene refrigeration unit.

FIGS. 2 through 6 show prior art processes for the recovery of olefins from a hydrocarbon feed stream. FIG. 2 shows a prior art arrangement for the separation of ethylene and ethane from one or more C2-rich hydrocarbon streams. The process can include an advanced deethanizer 106, an ethylene refrigeration compressor train 134, and an ethylene-ethane splitter 130. Hydrocarbon feeds 102, which comprises ethylene, ethane and C3's and heavier fees are supplied via one or more lines 104 to deethanizer 106. As used in the present specification and claims, an "advanced deethanizer" is one such as deethanizer 106, which separates the hydrocarbon feed to produce an ethylene rich overhead vapor 108, a mixed ethylene-ethane side stream 112, and a bottoms stream 110 comprising C3 and any heavier compounds present in the feed. Deethanizer 106 can include a heat exchanger 114 for reboiling.

The overhead ethylene stream 108 is supplied to condenser 116 and the condensate fed to reflux drum 118. Deethanizer 106 is refluxed with condensate from reflux drum 118, via line 119 and pumped with pump 120. Ethylene product from the deethanized system is supplied via line 124 to the either drum 136 of the ethylene refrigeration train 134 or send as product via line 153. This product from line 124 can be used a reflux to C2 splitter 130 either directly or via exchangers 150a and 147.

The ethylene-ethane splitter 130 is supplied with a mixed ethylene-ethane sidestream 112 from deethanizer 106. Line 112 generally includes control valves and a heat exchanger 128 to heat the mixed stream, as desired. The splitter 130 produces a substantially pure ethylene overhead stream 132, and a substantially pure ethane bottoms stream 146. The ethane bottoms stream 146 can be supplied via lines 148, 149 to heat exchangers 150a, 150b to reboil the splitter 130.

Ethylene refrigeration train 134 is supplied with ethylene vapor from the deethanizer overhead 108 via line 124, and the ethylene-ethane splitter overhead 132, and consists of at least one compressor 138, at least one heat exchanger condenser 140, and an accumulation drum 136. Splitter 130 is refluxed with ethylene liquid from drum 136 supplied via line 144, and the excess ethylene liquid is collected as product via line 152. Ethylene vapor from compressors 138 is typically used as a heat source to heat exchangers 150a for reboiling the splitter 130, supplied via line 142, and to side reboiler 147, if used. Additional reboiling is provided via exchanger 150b, if needed.

Figure 3:
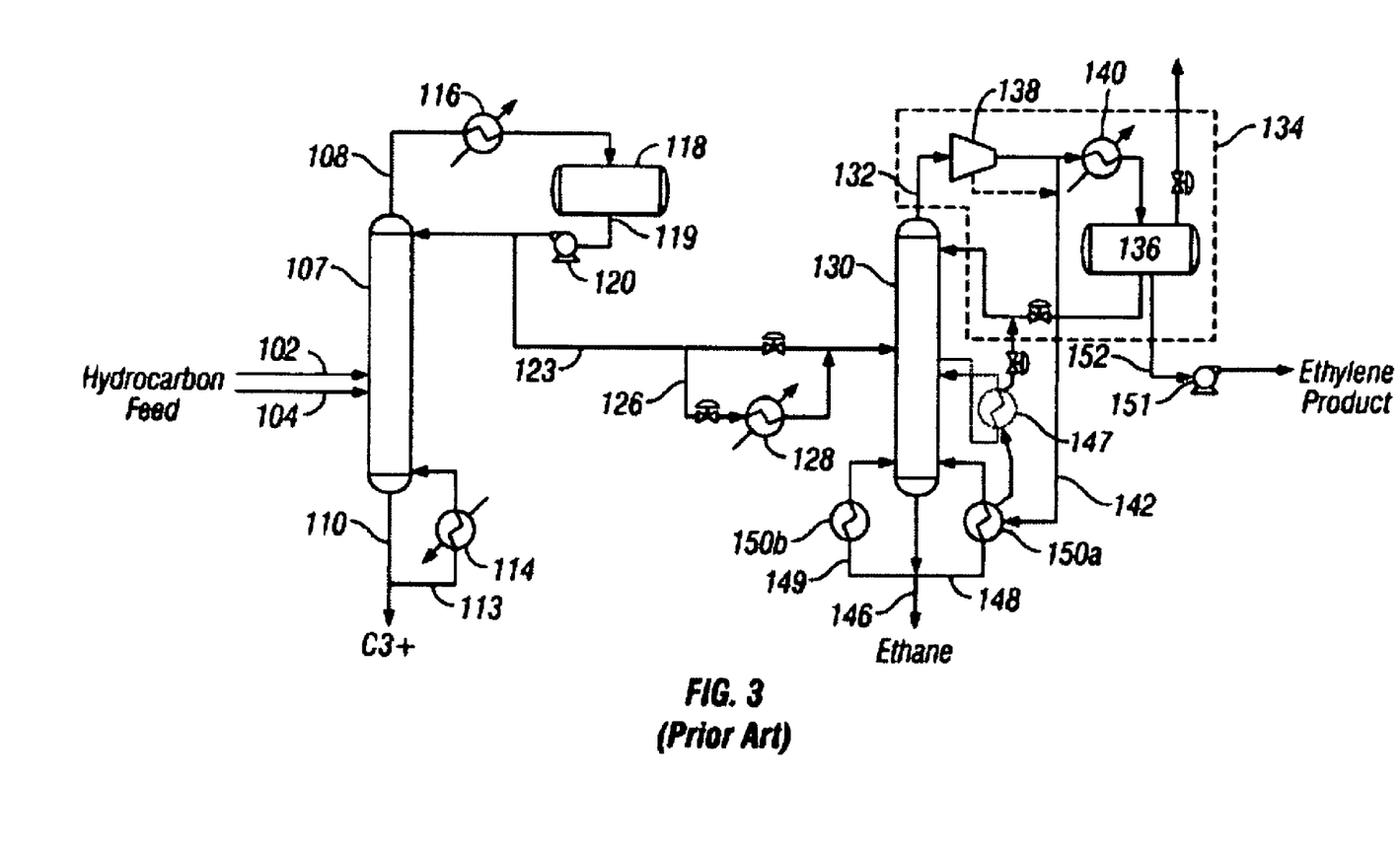
FIG. 3 is a schematic illustration of a prior art ethylene/ethane separation unit featuring a traditional deethanizer, an ethylene/ethane splitter, and an ethylene refrigeration unit.

As shown in FIG. 3, a prior art configuration for the separation of ethylene and ethane using a traditional deethanizer in a front-end depropanizer scheme front-end depropanized scheme refers to the olefins cold separation scheme wherein the first fractionating tower (after driers) is a depropanizer includes a deethanizer 107, an ethylene-ethane splitter 130, and an ethylene refrigeration compressor train 134. Hydrocarbon feeds 102, comprising ethane, ethylene, C3s and heavier hydrocarbons are supplied via one or more lines 104 to a deethanizer 107 to obtain an overhead vapor stream 108 consisting essentially of ethane and ethylene, and a bottoms stream 110 comprising C3 and heavier compounds. Heat is supplied to one or more heat exchangers 114 for reboiling deethanizer 107.

Overhead C2 stream 108 is supplied to condenser 116 and the condensate fed to reflux drum 118. Deethanizer 107 is refluxed with condensate from reflux drum 118, supplied via line 119 and pumped with pump 120. Ethylene/ethane condensate is supplied via line 123 to the ethylene-ethane splitter 130. If desired, line 123 may include heat exchangers 128 in stream 126, to heat or vaporize the splitter feed, as needed.

Ethylene-ethane splitter 130 produces an ethylene overhead vapor stream 132, which is supplied to the compressor 138 of the ethylene refrigeration compressor train 134, and a bottoms stream 146. Heat exchangers 150a and 150b are used for reboiling the splitter 130. The compressed ethylene vapor from ethylene compressor 138 is condensed in condenser 140, and fed to accumulator drum 136. A portion of the ethylene vapor from the compressor 138, is typically supplied via line 142 to heat exchangers 150 for reboiling the splitter 130, and to the heat exchanger of side reboiler 147, if used. Additional reboiling may be provided via one or more heat exchangers 150b. Splitter 130 can be refluxed with ethylene from drum 136 via line 144. Ethylene can be collected via line 151, supplied by pump 152. Ethane can be collected from the splitter 130 bottoms via line 146.

Figure 4:
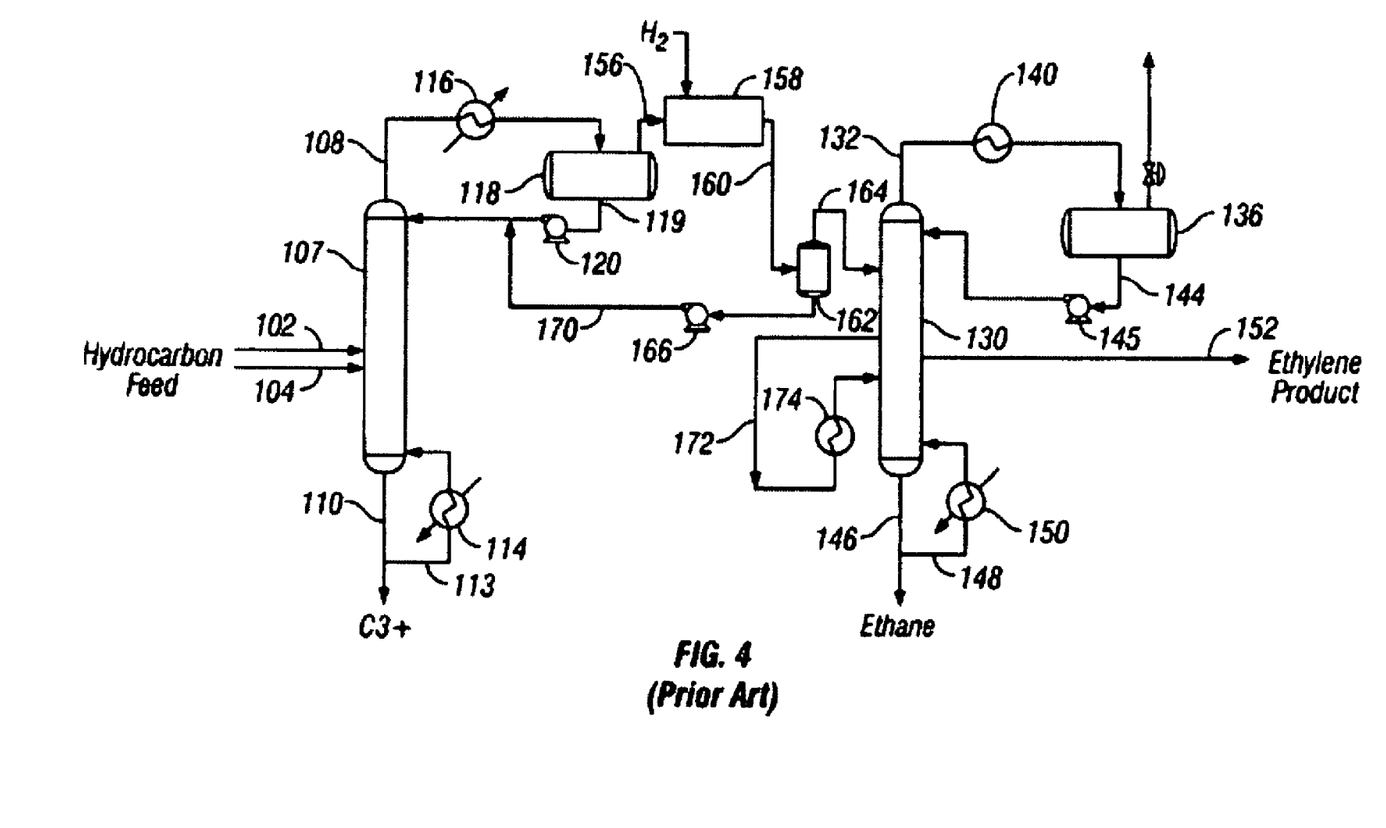
FIG. 4 is a schematic illustration of a prior art ethylene/ethane separation unit featuring a deethanizer, an acetylene converter system, and an ethylene/ethane splitter.

FIG. 4 shows a prior art ethylene-ethane separation process for a hydrocarbon feed in the front end high, or medium or low pressure demethanizer schemes. The process includes a deethanizer 107, acetylene converter system 158, and a splitter 130. One or more hydrocarbon feeds 102 are supplied to deethanizer 107 via line 104, to obtain an overhead vapor stream 108 comprising mainly of acetylene, ethylene, ethane and a bottoms stream 110 comprising and heavier compounds. The heat exchangers 114 are used for reboiling the deethanizer 107.

The deethanizer overhead stream 108 is partially condensed in condenser 116 and the condensate fed to reflux drum 118. Deethanizer 107 is refluxed with liquid supplied from reflux drum 118 via line 119 and pump 120. Vapor from reflux drum 118 is supplied via line 156 to acetylene converter system 158 for the removal and/or conversion of acetylene and then fed to drum 162. Drum 162 supplies vapor ethylene-ethane to the ethylene-ethane splitter 130, via line 164. The liquid collected in drum 162 can be pumped out as a product or returned to deetanizer 107 using Pump 166.

Splitter 130 produces essentially a pure ethylene overhead vapor stream 132 and a bottoms stream 146 consisting primarily of ethane. The overhead vapor 132 is condensed with condenser 140 and collected in drum 136. Pump 145 supplies the condensed ethylene from drum 136 to reflux splitter 130 via line 144. Ethylene product is exported via line 152. Splitter 130 includes heat exchangers 150 for reboiling, and can also include a side reboilers 174 via line 172.

Figure 5:
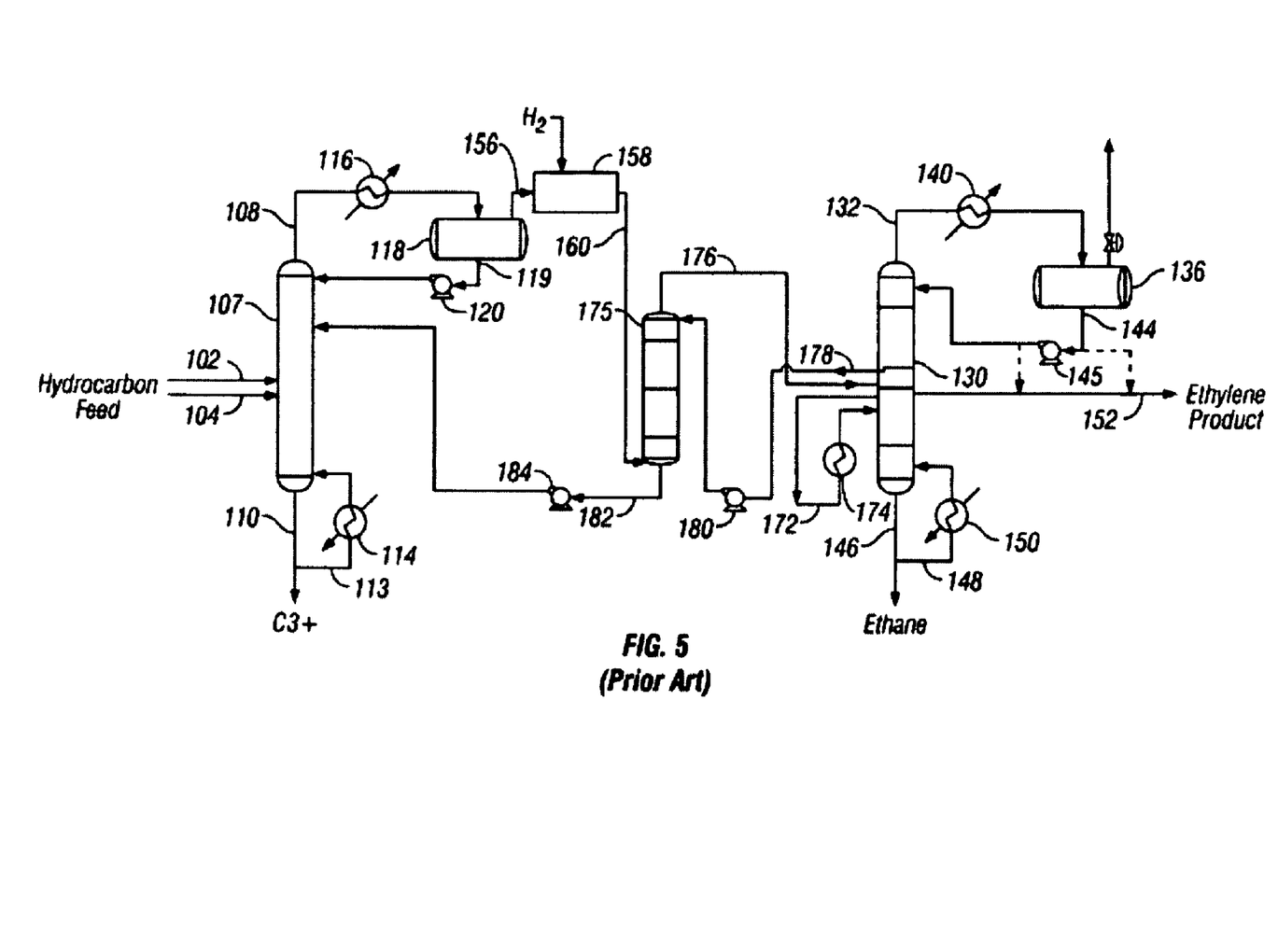
FIG. 5 is a schematic illustration of a prior art ethylene/ethane separation unit featuring a deethanizer, an acetylene converter system, a green oil wash tower, and an ethylene/ethane splitter.

Another prior art process for the separation of ethylene, ethane and C3+ from hydrocarbon streams is shown in FIG. 5 for a front end demethanizer scheme. The process includes green oil for removal of impurities and undesired side products produced in the acetylene converter system. The process includes a deethanizer 107, an ethylene/ethane splitter 130, and a green oil removal system, for example wash tower 175. One or more hydrocarbon feeds 102 comprising acetylene, ethane, ethylene and C3+ is supplied to deethanizer 107 via one or more lines 104, producing an overhead effluent 108, comprising mainly of acetylene, ethane and ethylene, and a bottoms stream 110 comprising C3 and heavier compounds. The heat exchangers are used 114 for reboiling deethanizer 107 which may also employ side reboiler(s) as is known in the art. The C3 and heavier compounds are fed to a depropanizer (not shown), or exported for otherwise including cracking.

Overhead effluent 108 is supplied to condenser 116 to partially condense the C2's stream, which is phase separated in reflux drum 118. Liquid hydrocarbons are supplied to reflux the deethanizer 107 via line 119 and pump 120. Vapor from reflux drum 118 is supplied via line 156 to an acetylene converter system 158, and via line 160 to green oil removal wash tower 174. The wash tower overhead 176 is supplied to ethylene-ethane splitter 130. The wash tower bottoms stream 182 can be pumped via Pump 184 to deethanizer 107.

Splitter 130 produces an overhead stream 132 comprising nearly pure ethylene and a bottoms stream 146 consisting primarily of ethane. The heat exchangers 150 are used for reboiling the splitter 130. A sidestream from splitter 130 may be supplied to reflux the green oil wash tower 174 via line 178, fed via pump 180. Overhead stream 132 is condensed in condenser 140 and fed to accumulation drum 136. Splitter 130 is refluxed with liquid ethylene from drum 136, supplied to the splitter by pump 145 via line 144. Ethylene can be collected via line 152, and ethane can be collected via line 146.

Figure 6A:
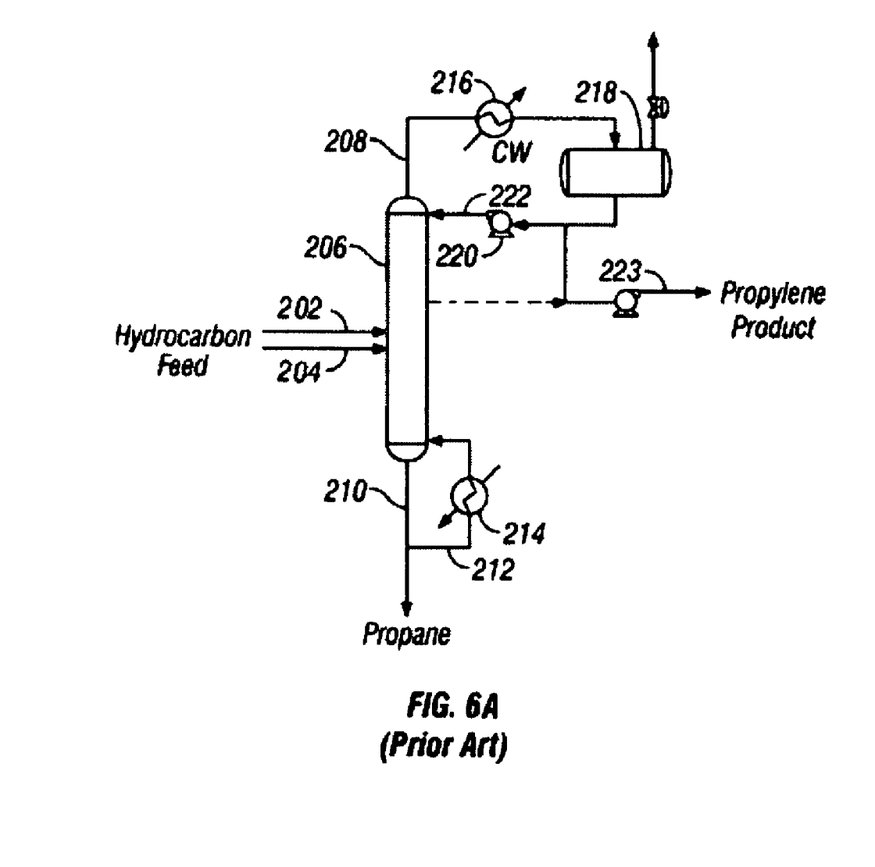
FIG. 6a and FIG. 6b depict schematic illustrations of a prior art propane/propylene separation unit featuring a C3 splitter and a separate propylene refrigeration unit.
Figure 6B:
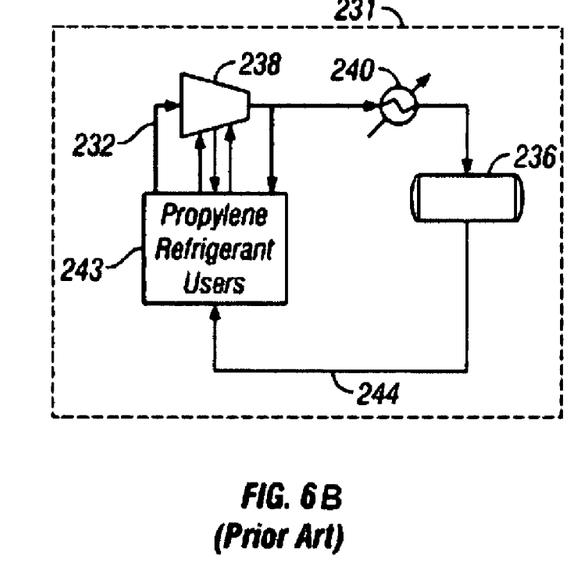

A prior art propylene-propane arrangement is shown in FIG. 6a and FIG. 6b. The arrangement includes one or more hydrocarbon feed streams 202 comprising propane and propylene supplied via one or more lines 204 to a propylene-propane splitter 206. The splitter 206 produces an overhead stream 208 consisting essentially of propylene and a bottoms stream 210 consisting essentially of propane. The heat exchanger 214 is used for reboiling the splitter. Overhead vapor stream 208, comprising primarily propylene, can be supplied to condenser 216, which is be a chilled water condenser, condensing the propylene for collection in drum 218. The splitter 206 is refluxed with propylene supplied by pump 220 via line 222, and excess propylene is collected via line 223. The propylene refrigeration compressor train 231 is typically a separate utility and including at least one compressor system 238, at least one exchanger as a condenser 240, an accumulation drum 236, and a line 244 for supplying propylene as refrigerant to additional propylene consumer(s) 243. Line 232 can resupply the heated and expanded propylene to the compressor 238.

BRIEF DESCRIPTION OF THE DRAWINGS

The detailed description will be better understood in conjunction with the accompanying drawings as follows.

The embodiments are detailed below with reference to the listed Figures.

DETAILED DESCRIPTION OF THE EMBODIMENTS

Before explaining the embodiments in detail, it is to be understood that the embodiments are not limited to the particular embodiments and that they can be practiced or carried out in various ways.

The embodiments integrate an olefin fractionation column with an olefin refrigeration system to reduce the hydrocarbon inventory, required equipment and associated costs. The processes and apparatus supply the overhead olefin effluent from a fractionation column directly to the associated refrigeration system, thereby eliminating condensers reflux drums ethylene pumps normally associated with typical fractionation processes.

Embodied processes for separating a light hydrocarbon stream with at least one alkane component and at least one olefin component are provided. The embodied processes can include supplying the light hydrocarbon streams to a fractionation column to obtain an overhead olefin vapor stream, supplying a plurality of olefin refrigerant vapor streams to an olefin refrigeration compressor train, wherein one of the said plurality of streams comprises the overhead olefin vapor stream from the fractionation column, cooling and condensing olefin refrigerant from the olefin refrigeration compressor train to obtain liquid olefin refrigerant, refluxing the fractionation column with a first portion of the liquid olefin refrigerant, using a second portion of the liquid olefin refrigerant to form at least one olefin refrigerant vapor stream for the supply to the olefin refrigerant compressor train and recovering a third portion of the liquid olefin refrigerant as an olefin product stream.

The light hydrocarbon stream can comprise propane and propylene, and the fractionation column can be a propane-propylene splitter. The light hydrocarbon stream can comprise ethane, ethylene, and C3's and the fractionation column can comprise an advanced deethanizer with the first portion of liquid olefin refrigerant refluxing deethanizer column and another portion refluxing an ethylene-ethane splitter. The processes can comprise heat pumping the ethylene-ethane splitter with ethylene from the ethylene refrigeration compressor train. The processes can comprise supplying a portion of the olefin refrigerant to additional refrigerant consumers for refrigeration, and returning olefin refrigerant vapor from the additional refrigerant consumers to the olefin refrigeration compressor train.

Embodied processes for deethanizing a light hydrocarbon stream comprising olefins can include supplying at least one light hydrocarbon stream comprising ethylene, ethane and C3's to a deethanizer, feeding a side stream of ethylene and ethane from the deethanizer to an ethylene-thane splitter, supplying ethylene vapor from the deethanizer and splitter to an ethylene refrigeration compressor train to form ethylene liquid, refluxing the deethanizer and splitter with a portion of the ethylene liquid from the refrigeration train, recovering and exporting a portion of the ethylene liquid from the refrigeration train, recovering ethane liquid from the splitter, and recovering C3+ from deethanized bottom.

The processes can comprise heat pumping the ethylene-ethane splitter with ethylene from the ethylene refrigeration compressor train. The processes can comprise supplying a portion of the ethylene liquid from the ethylene refrigeration compressor train to additional refrigeration consumers. The processes can comprise returning ethylene vapor from the additional refrigeration consumers to the ethylene refrigeration compressor train.

Embodied apparatus for deethanizing light hydrocarbons can include a line to feed a hydrocarbon stream comprising ethane and ethylene to a deethanizer, a line to supply an ethylene-ethane side draw from the deethanizer to an ethylene-ethane splitter, lines for supplying ethylene vapors from the deethanizer and the splitter to an ethylene refrigeration compressor train, lines for refluxing the deethanizer and splitter with liquid ethylene from the refrigeration compressor train, a first product line for collecting liquid ethane from the splitter, and a second product line for collecting liquid ethylene from the ethylene refrigeration compressor train.

The apparatus can further comprise a line for heat pumping the splitter with ethylene from the ethylene refrigeration compressor train. The apparatus can comprise lines to supply ethylene liquid to a plurality of refrigeration consumers and to return ethylene vapor from the refrigeration consumers to the ethylene refrigeration compressor train.

Embodied apparatus for separating a hydrocarbon stream comprising at least one alkane component and at least one olefin component is provided, can include means for supplying the hydrocarbon stream to a fractionation column to obtain an overhead olefin vapor stream, means for supplying a plurality of olefin refrigerant vapor streams to refrigeration compressor train, wherein one of the said plurality of streams comprises the overhead vapor stream from the fractionation column, means for chilling and condensing vapor from the refrigeration compressor train to obtain liquid refrigerant, means for refluxing the fractionation column with a first portion of the liquid olefin refrigerant, using a second portion of the liquid refrigerant to form at least one refrigerant vapor stream for the supply to the refrigerant compressor train, and means for recovering a third portion of the liquid refrigerant as an product stream.

Embodied methods for retrofitting an advanced deethanizer for operating the deethanizer without an overhead condenser, reflux drum or reflux pump is provided, can include providing an advanced deethanizer to receive a hydrocarbon feed stream comprising ethane and ethylene to obtain an overhead ethylene vapor stream, an overhead condenser for the ethylene vapor stream, an ethylene-ethane splitter supplied with a side draw from the deethanizer to obtain ethylene overhead vapor and ethane bottom streams, and an ethylene refrigeration compressor train, wherein the compressor train is supplied with the ethylene overhead vapor stream from the splitter, installing a line to bypass the overhead condenser and supply the overhead ethylene vapor stream from the deethanizer to the ethylene refrigeration compressor train, and installing a line from the refrigeration compressor train to supply liquid ethylene to reflux the deethanizer.

Embodied improvements for processes for recovering olefins from a cracking furnace effluent, comprising compression of the effluent and fractionation in a demethanizer, deethanizer, depropanizer, debutanizer, ethylene-ethane splitter and propane-propylene splitter, to obtain purified streams of at least ethane, ethylene, propane and propylene, are provided herein. These embodied improvements can include supplying at least one light hydrocarbon stream comprising ethylene and ethane to the deethanizer, feeding a side stream of ethylene and ethane from the deethanizer to the ethylene-ethane splitter, supplying ethylene vapor from the deethanizer and splitter to an ethylene refrigeration compressor train to form ethylene liquid, and refluxing the deethanizer and splitter with a portion of ethylene liquid from the refrigeration train.

Embodied improvements for processes for recovering olefins from a cracking furnace effluent comprising compression of the effluent and fractionation in a demethanizer, deethanizer, depropanizer, debutanizer, ethylene-ethane splitter and propane-propylene splitter, to obtain purified streams of at least ethane, ethylene, propane and propylene are included herein. The embodied improvements can include feeding at least one light hydrocarbon stream comprising ethylene and ethane to the deethanizer to obtain an ethylene-ethane overhead vapor stream, supplying the overhead vapor stream from the deethanizer to the ethylene-ethane splitter to obtain an overhead ethylene vapor stream, supplying the ethylene vapor stream from the splitter to an ethylene refrigeration compressor train to obtain ethylene liquid, refluxing the ethylene-ethane splitter with the ethylene liquid, refluxing the deethanizer with a liquid sidedraw from the splitter, and recovering and exporting a portion of the ethylene refrigerant.

The improvements can include heat pumping the ethylene-ethane splitter with ethylene from the ethylene refrigeration compressor train. The improvements can include comprising supplying a portion of the ethylene liquid to additional refrigeration consumers for refrigeration, and returning ethylene vapor from the additional refrigeration consumers to the ethylene refrigeration compressor train.

The improvements and processes can comprise a front end depropanizer scheme, and the overhead ethane-ethylene vapor stream can be supplied from the deethanizer directly to the ethylene-ethane splitter and the liquid sidedraw from the splitter can be pumped directly to the deethanizer.

The improvements and processes can comprise a front end high pressure demethanizer scheme, and the overhead vapor stream can be supplied from the deethanizer directly to a acetylene converter system, through a liquid accumulator drum and then to the ethylene-ethane splitter, and the liquid sidedraw from the splitter can be pumped to the accumulator and then from the accumulator to the deethanizer. The process can comprises a front end standard pressure demethanizer scheme, the overhead vapor stream can be supplied from the deethanizer directly to a acetylene converter system, through a green oil wash tower in contact with a portion of the splitter sidedraw and then to the ethylene-ethane splitter, and the splitter sidedraw can be pumped to the green oil wash tower and to the deethanizer. A sidestream of the splitter sidedraw can be pumped to the green oil wash tower and then from the green oil wash tower to the deethanizer.

The embodied processes, in general, provide for the recovery of olefins and alkanes from a hydrocarbon feed stream. Olefin vapors from a fractionation column can be supplied directly to an olefin refrigeration system, eliminating the need for the condenser, reflux drum and pumps typically associated with a fractionation column. The olefins recovery processes can be effective for use in ethylene and propylene plants.

Various fractionation methods and apparatuses can be used in separating a furnace effluent into its component parts, including but not limited to, a demethanizer, a deethanizer, an ethylene-ethane separator (hereinafter C2 splitter), a depropanizer, a propane-propylene separator (C3 splitter), etc. Methane separation is desirably performed with a demethanizer, but can be a solvent absorption/regeneration unit, or any other process capable of separating methane and lighter components from a hydrocarbon stream.

In the separation of the various hydrocarbon fractions, refrigeration is typically employed to facilitate the process. Typical refrigeration systems can include several levels of olefin refrigerant (i.e. streams of progressively decreasing temperature), for a variety of refrigeration processes. Thus, refrigeration units typically include multiple heat exchangers, coolers, compressors, and flash drums depending upon the feed being supplied.

The hydrocarbon effluent produced in a furnace or cracking process typically can comprise olefins, such as for example, ethylene, propylene, butadiene, and alkanes, such as for example, methane, ethane, propane, and butane. The effluent can also include heavier hydrocarbons, as well as other light components, such as for example, hydrogen, carbon dioxide, and carbon monoxide. The composition of the raw effluent stream depends on several different factors, including but not limited to, feedstock type, steam content, conversion rate, and furnace or catalytic cracker temperature, pressure, residence time, and severity.

Figure 1:
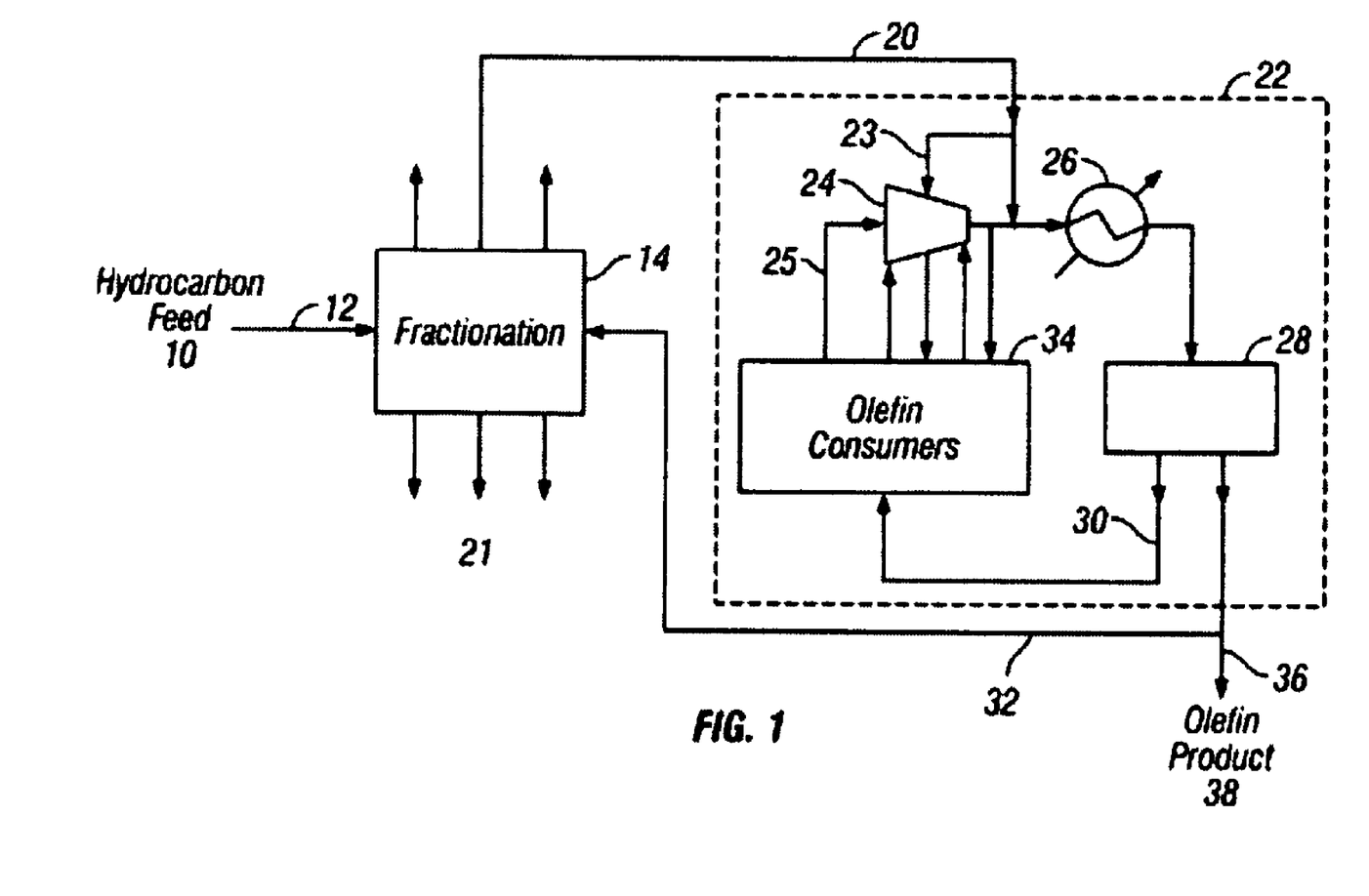
FIG. 1 depicts a schematic illustration of one embodiment, wherein an olefin refrigeration unit is integrated into an alkane/olefin separation process.

With reference to the figures, FIG. 1 depicts a schematic illustration of one embodiment, wherein an olefin refrigeration unit is integrated into an alkane/olefin separation process. A light hydrocarbon stream 10 is supplied via line 12 to a fractionation process 14. For purposes of this example, a light hydrocarbon stream is defined as a stream comprising C5 and lighter hydrocarbons. The fractionation process 14 can include a deethanizer, depropanizer, ethylene-ethane splitter, propane-propylene splitter, or the like, depending on the feedstock. The fractionation process 14 can separate the hydrocarbon feed into a plurality of overhead streams including overhead olefin vapor stream 20 and a plurality liquid bottoms streams 21. The overhead olefin vapor stream 20 can be supplied to the olefin refrigeration system 22.

Depending on the pressure and temperature, the olefin vapor stream 20 can be fed to a stage in compressor 24 via line 23, or fed to chiller/condenser 26 to provide a liquid olefin stream which can be supplied to accumulator drum 28. A portion of the liquid olefin can be provided as refrigerant for alternate refrigerant consumers 34 via line 30, or a column in fractionation process 14 can be refluxed with a portion of the olefin liquid, supplied via line 32. Olefin product 38 can be collected via line 36. Olefin refrigerant liquid vaporized by refrigerant consumers 34 can be returned to compressor 24 of the refrigeration train 22 to complete the cycle. Refrigerant consumers 34 can use the refrigerant for refluxing a fractionation column, or as a refrigerant for the heating or cooling of a process stream or unit operation. The olefin refrigeration system 22 can include multiple condensers and compressors, as desired and necessary, and is well known in the art.

Fractionation columns, (for example, a deethanizer or depropanizer) can contain a plurality of vertically spaced trays, one or more packed beds, or a combination of trays and beds. The distillation column may consist of two sections. The bottom section can include reboilers that heat and vaporize portions of the liquids flowing down the column to provide stripping vapors which flow up the column. Desirably, for the separation of a feed comprising ethane and ethylene, the fractionation column can be an advanced deethanizer. As used herein, an advanced deethanizer refers to a deethanizer wherein the feed is separated into an overhead ethylene effluent, an ethylene/ethane sidedraw stream and a bottoms stream comprising ethane. The mixed sidedraw stream can be further fractionated in a C2 splitter to recover ethylene and ethane and a liquid sidedraw from the splitter can be returned to reflux the deethanizer.

Figure 7:
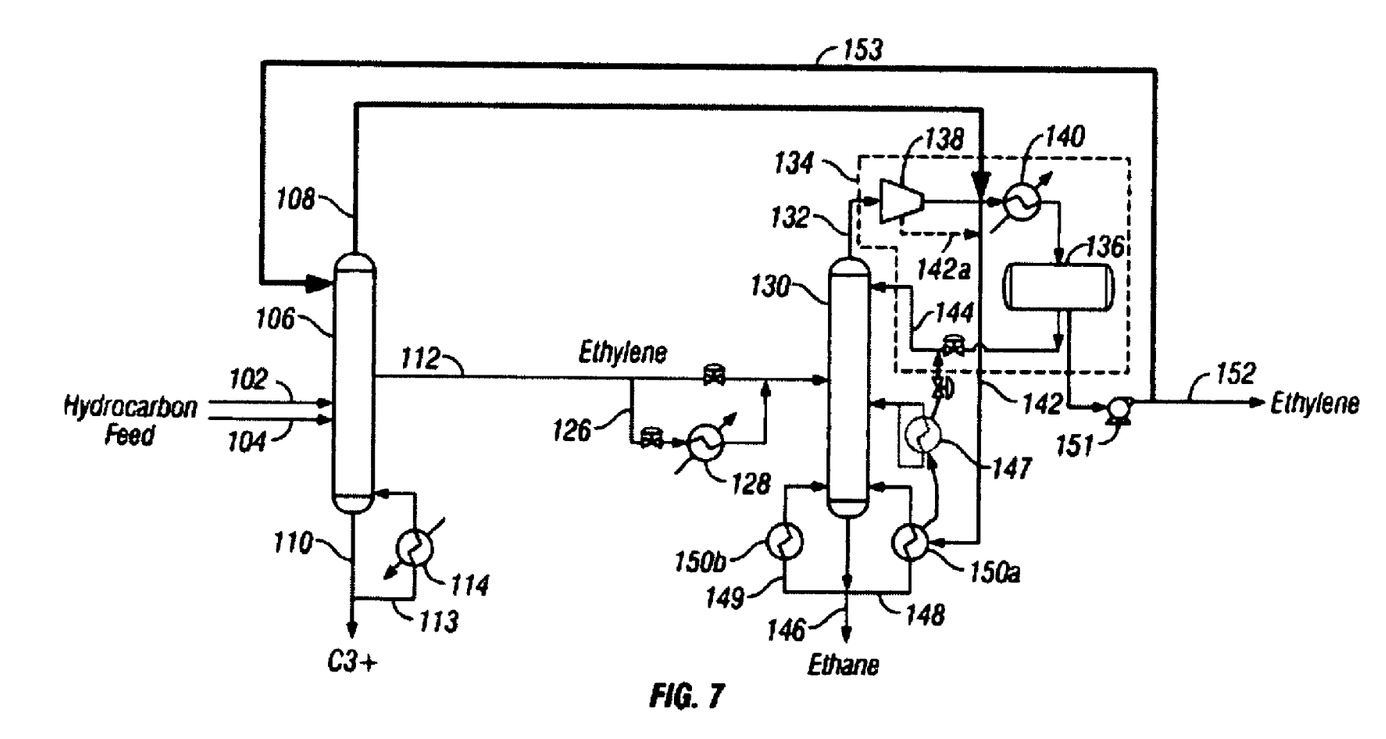
FIG. 7 depicts a schematic illustration of one embodiment, wherein an ethylene refrigeration unit has been integrated into an ethylene recovery process corresponding to FIG. 2, wherein the deethanizer overhead is supplied directly to the refrigeration train, and wherein the deethanizer is refluxed with ethylene liquid from the refrigeration unit.

FIG. 7 depicts a schematic illustration of one embodiment, wherein an ethylene refrigeration unit has been integrated into an ethylene recovery process corresponding to FIG. 2, wherein the deethanizer overhead is supplied directly to the refrigeration train, and wherein the deethanizer is refluxed with ethylene liquid from the refrigeration unit. As exampled, the process can include an advanced deethanizer 106, an ethylene refrigeration compressor train 134, and an ethylene-ethane splitter 130. Hydrocarbon feeds 102, which can comprise ethylene and ethane, can be supplied via lines 104 to deethanizer 106. Deethanizer 106 can separate the hydrocarbon feed, producing an ethylene rich overhead vapor 108, a mixed ethylene-ethane side stream 112, and a bottoms stream 110 comprising C3 and heavier compounds. The bottoms stream 110 can be supplied to a heat exchanger 114 for reboiling via line 113 if desired.

The overhead 108 can be supplied to an ethylene refrigeration compressor train 134, thereby eliminating the need for condenser 116 and reflux drum 118, as exampled in the prior art process of FIG. 2. The ethylene refrigeration compressor train 134 can comprise at least one compressor 138, at least one heat exchanger condenser 140, and an accumulation drum 136. The deethanizer 106 can be refluxed with ethylene liquid supplied from the drum 136 via line 153 and pumped with pump 151. The ethylene-ethane splitter 130 can be refluxed with liquid ethylene from drum 136, supplied via line 144.

The ethylene-ethane splitter 130 can be supplied with a mixed ethylene-ethane sidestream 112 from deethanizer 106. Line 112 can include splitstream 126 and control valves and a heat exchanger 128 to heat the mixed stream, as desired. The splitter 130 can produce a substantially pure ethylene overhead stream 132, and a substantially pure ethane bottoms stream 146. The ethane bottoms stream 146 can be supplied via lines 148, 149 to heat exchangers 150a, 150b to reboil splitter 130.

The ethylene refrigeration train 134 can be supplied with ethylene vapor from the deethanizer overhead line 108 and ethylene-ethane splitter overhead 132. The ethylene liquid can be collected from drum 136 as product via line 152. If desired, ethylene vapor from compressors 138 can be supplied as heat source for heat exchangers 150a for reboiling the splitter bottoms 146, supplied via line 142, and optionally as a heat source for side reboiler 147. Additional reboiling can be provided by heat exchanger 150b, if needed. If desired, a portion of the ethylene liquid from the refrigeration compressor train 134 can be exported to additional refrigeration consumers, for use as a refrigeration source. The additional refrigeration consumers return ethylene vapor to the refrigeration compressor train 134 to complete the refrigeration cycle.

To handle a larger volume of ethylene, the present invention can employ a larger accumulation drum 136 for the refrigeration system 134 than is typically provided in the prior art separation process of FIG. 2 wherein the deethanizer 106 includes a condenser 116 and reflux drum 118. Total hydrocarbon inventory for the process can be decreased through the elimination of the condenser 116 and reflux drum 118.

The exampled process of FIG. 7 can be applied as a retrofit method to an existing advanced deethanizer. Optionally, retaining the existing equipment, the overhead line 108 can be conveniently installed to connect directly to the refrigeration compressor train 134, with a valve (not shown) allowing the deethanizer condenser 116 and reflux drum 118 to be utilized if necessary. A second line 153 to supply ethylene from the refrigeration compressor train 134 directly to the deethanizer 106 can be installed for refluxing the deethanizer 106.

A demethanizer (and a demethanized prestripper) can be employed upstream from the deethanizer 106, generally being used to remove methane, carbon dioxide, and hydrogen. The demethanizer can produce a bottoms product essentially free of methane and lighter components as these are recovered as an overhead effluent stream, while the C2 and heavier materials are recovered as a bottoms product.

Figure 8:
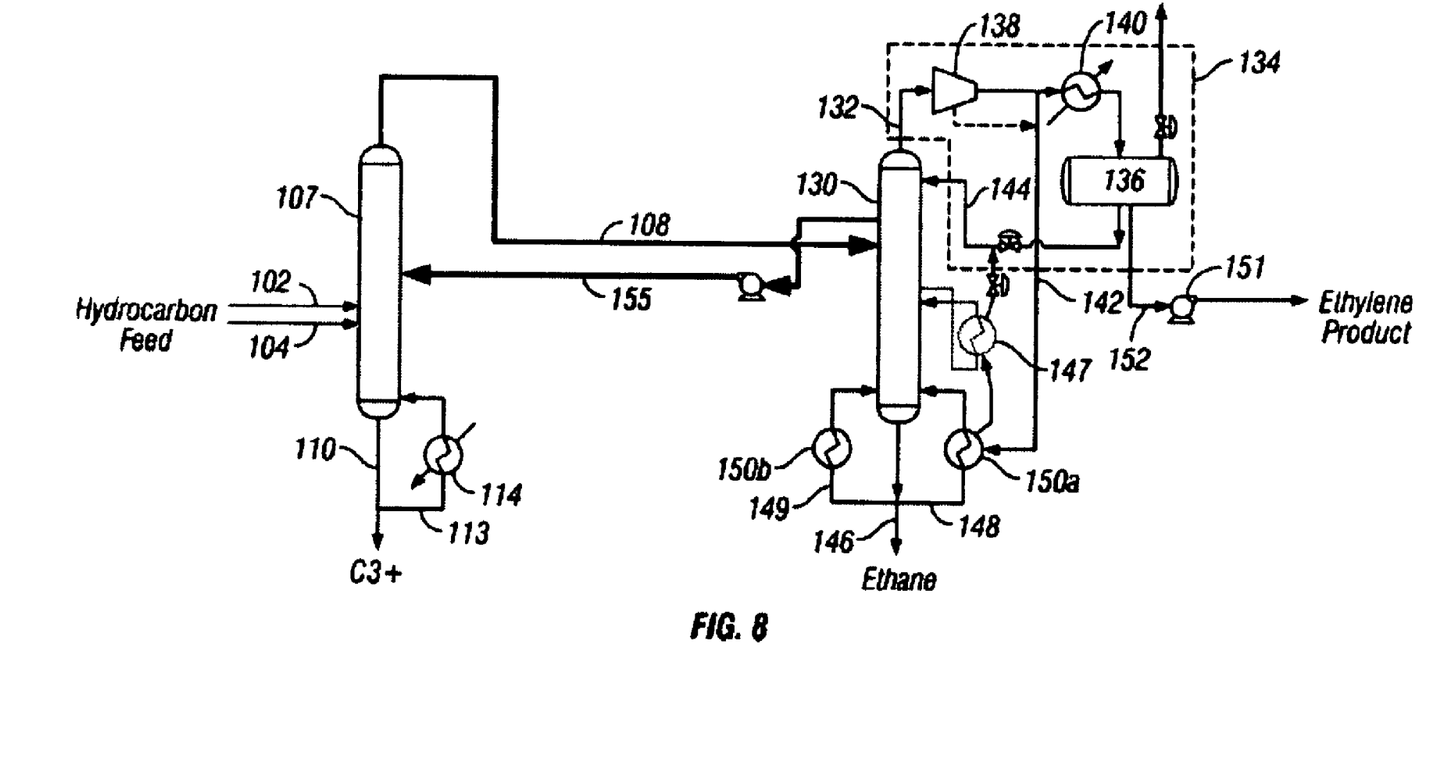
FIG. 8 depicts a schematic illustration of one embodiment, wherein an ethylene refrigeration unit has been integrated into an ethylene recovery process corresponding to FIG. 3, wherein the deethanizer overhead is supplied directly to the ethylene/ethane splitter and the deethanizer is refluxed with a sidestream from the splitter.

FIG. 8 depicts a schematic illustration of one embodiment, wherein an ethylene refrigeration unit has been integrated into an ethylene recovery process corresponding to FIG. 3, wherein the deethanizer overhead is supplied directly to the ethylene/ethane splitter and the deethanizer is refluxed with a sidestream from the splitter. The process can include a deethanizer 107, an ethylene-ethane splitter 130, and an ethylene refrigeration compressor train 134. Light hydrocarbon feeds 102 can be supplied via lines 104 to deethanizer 107 to obtain an overhead vapor stream 108 comprising ethane and ethylene, and a bottoms stream 110 comprising C3 and heavier compounds. The bottoms stream 110 can be supplied to heat exchanger 114 via line 113 for reboiling deethanizer 107. The process depicted in FIG. 8 can be applicable when the hydrocarbon stream(s) 102, 104 do not contain acetylene in processes which use front end acetylene converter and front end depropanizer.

The overhead stream 108 can be supplied to the ethylene-ethane splitter 130 to produce an ethylene vapor overhead stream 132 and an ethane liquid bottoms stream 146. The ethylene overhead stream 132 can be compressed in the ethylene refrigeration compressor train 134 compressor 138, chilled in condenser 140, and collected in accumulation drum 136. If desired, a portion of the ethylene vapor from the compressor can be supplied via line 142 to heat exchanger 150a for reboiling the splitter 130, and optionally to side reboiler 147. Additional reboiling can be provided via heat exchanger 150b. A mixed ethylene/ethane sidestream 155 can be supplied from splitter 130 to reflux deethanizer 107. Splitter 130 can be refluxed with ethylene liquid from accumulation drum 136. Ethylene liquid can be collected from drum 136 via pump 151 and line 152. Ethane can be collected from splitter 130 via line 146.

By eliminating the deethanizer condenser 116 and reflux drum 118 employed in the prior art process of FIG. 3, the size of the ethylene refrigeration compressor train condenser 140 may need to be increased to accommodate the increased ethylene volume.

Figure 9:
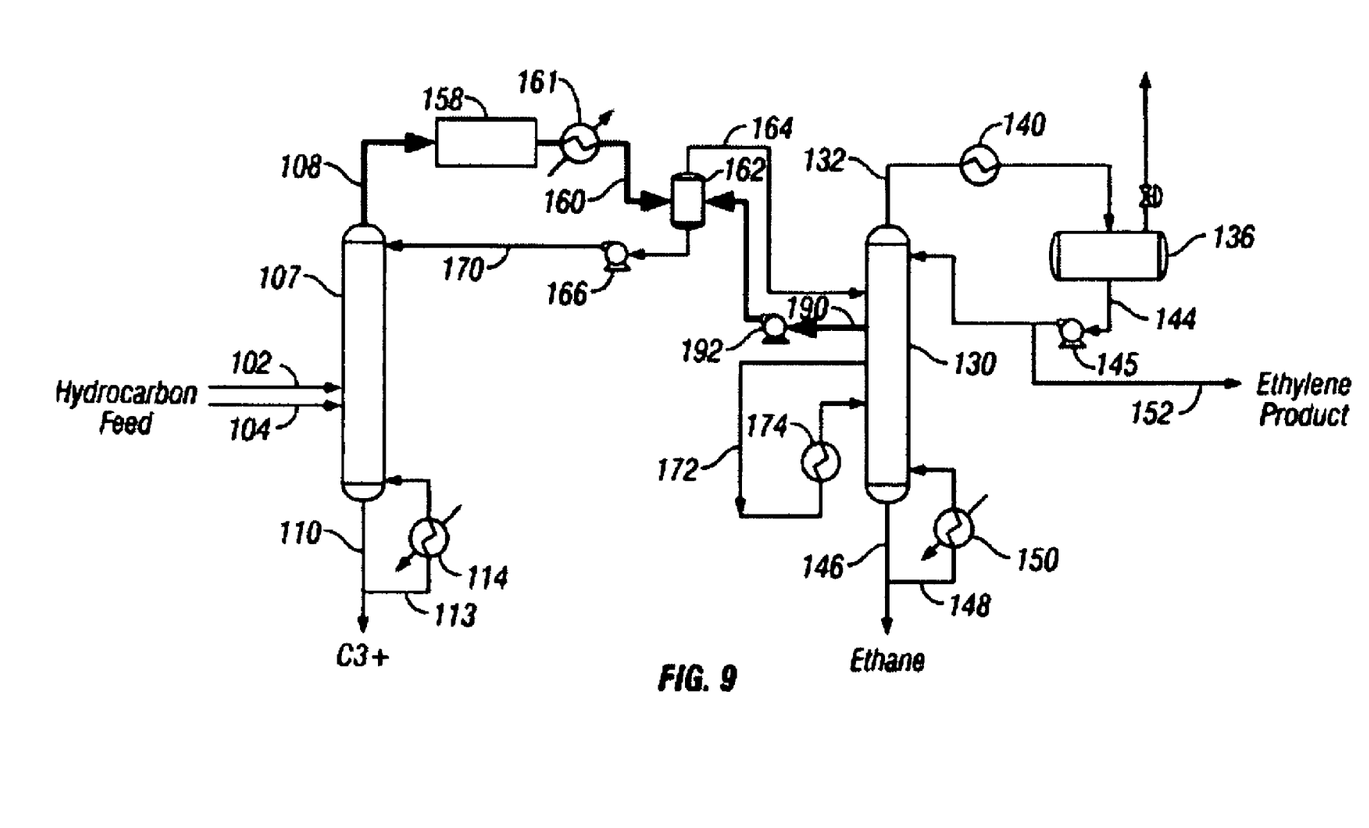
FIG. 9 depicts a schematic illustration of one embodiment, wherein the deethanizer condenser and reflux drum are removed, and wherein the deethanizer overhead is supplied directly to the acetylene converter system, in an ethylene recovery process according to FIG. 4.

FIG. 9 depicts a schematic illustration of one embodiment, wherein the deethanizer condenser and reflux drum are removed, and wherein the deethanizer overhead is supplied directly to the acetylene converter system, in an ethylene recovery process according to FIG. 4. The exampled process can provide a method for ethylene/ethane separation of a hydrocarbon feed in a front end demethanizer scheme. The process can include a deethanizer 104, an acetylene converter 158 and an ethylene/ethane splitter 130. The hydrocarbon feeds 102 can be supplied to the deethanizer 107 via lines 104 to obtain an overhead vapor stream comprising acetylene, ethylene and ethane, and a bottoms stream 110 comprising C3 and heavier compounds. The deethanizer 107 can be reboiled by supplying a portion of the bottoms stream 110 to heat exchanger 114 via line 113.

The deethanizer overhead vapor stream 108 can be supplied to the acetylene converter system 158 for the removal of acetylene. The converter system 158 effluent can exit via line 160, which may include a condenser 161, and supplies drum 162. Condenser 161 can be used during start up to reduce flaring, but is desirably not used during steady state operations. Vapor from drum 162 can be supplied to the ethylene-ethane splitter 130. Liquid from drum 162 can be used to reflux deethanizer 107, supplied via line 170 and pump 166.

Ethylene/ethane splitter 130 can produce an overhead vapor stream 132 comprising primarily ethylene, and a bottoms stream 146 comprising primarily ethane. The overhead vapor 132 can be condensed in condenser 140 and fed to accumulation drum 136. Pump 145 can supply condensed ethylene via line 144 to reflux the splitter 130, or can supply the condensed ethylene via line 152 for export. The splitter 130 can include a heat exchanger 174 fed by line 172 for side reboiling, and can also include heat exchanger 150 supplied with a portion of the bottoms stream 146 via line 148 for reboiling. A sidedraw 190 from splitter 130 can be supplied by pump 192 to drum 162.

Due to the elimination of the deethanizer condenser 116 and reflux drum 118 from the prior art design, the size of condenser 140 and the side reboiler 174 may be increased in size to accommodate the additional ethylene and ethane volumes.

Figure 10:
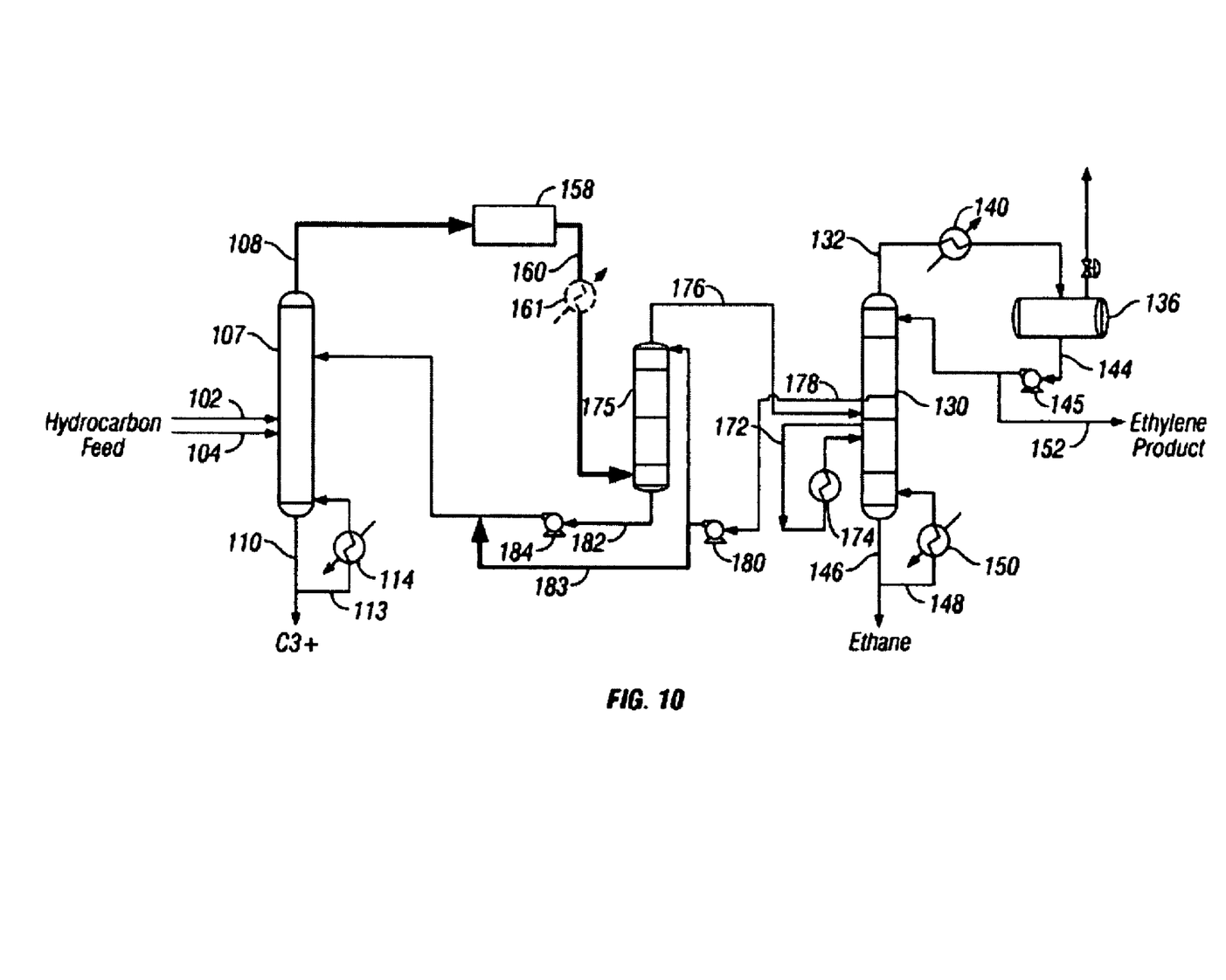
FIG. 10 depicts a schematic illustration of one embodiment, wherein the deethanizer condenser and reflux drum are removed, the deethanizer overhead is supplied directly to an acetylene converter system and the green oil wash tower, and wherein a portion of the side stream from the splitter is supplied to the green oil wash tower (and to deethanizer), in an ethylene recovery process according to FIG. 5.

FIG. 10 depicts a schematic illustration of one embodiment, wherein the deethanizer condenser and reflux drum are removed, the deethanizer overhead is supplied directly to an acetylene converter system and the green oil wash tower, and wherein a portion of the side stream from the splitter is supplied to the green oil wash tower (and to deethanizer), in an ethylene recovery process according to FIG. 5. This example process can include a deethanizer 107, an acetylene converter system 158, a green oil wash tower 175, and an ethylene/ethane splitter 130. Hydrocarbon feeds 102 comprising acetylene, ethylene and ethane can be supplied to deethanizer 107 via line 104, producing an overhead effluent 108, comprising acetylene, ethylene and ethane, and a bottoms stream 110 comprising C3 and heavier compounds. The bottoms stream 110 can be fed via line 113 to heat exchanger 114 for reboiling deethanizer 107. The bottoms stream comprising C3 and heavier compounds can be fed to a depropanizer, or exposed.

The deethanizer overhead vapor 108 can be supplied to the acetylene converter system 158, reducing the acetylene concentration of the overhead effluent, and can be fed via line 160 to condenser 161, which can be used on startup to reduce flaring. The condenser 161 can be relatively small, as compared with the prior art overhead condenser 116, which has been eliminated in this embodiment of the invention. The effluent can be supplied to green oil wash tower 175, producing an overhead vapor which is supplied via line 176 to the ethylene/ethane splitter 130. Wash tower bottoms are supplied via line 182 and pump 184 to deethanizer 107.

The splitter 130 can produce an overhead effluent 132 comprising primarily ethylene, which can be supplied to condenser 140 and accumulation drum 136. The splitter 130 can produce a bottoms stream 146 comprising primarily ethane, which can be supplied to heat exchanger 150 via line 148 for reboiling the splitter 130. The splitter 130 can be refluxed with ethylene liquid from accumulation drum 136, supplied via line 144 (after chilling if desired). Liquid ethylene can be collected as product via line 152, and liquid ethane can be collected as product via line 146. Splitter 130 can include a side reboiler comprising line 172 and exchanger 174. Splitter 130 can supply a sidedraw 178 to reflux the green oil wash tower 175. A portion of the sidedraw 178 can be directly supplied to reflux the deethanizer 107 via line 183.

To accommodate the additional volume of ethylene, the splitter condenser 140 and splitter side reboiler 174 can be increased in size. Similarly, green oil wash tower pumps 180 and 184 can be increased in size to compensate for the elimination of reflux pump 120 found in the prior art process of FIG. 5.

Figure 11:
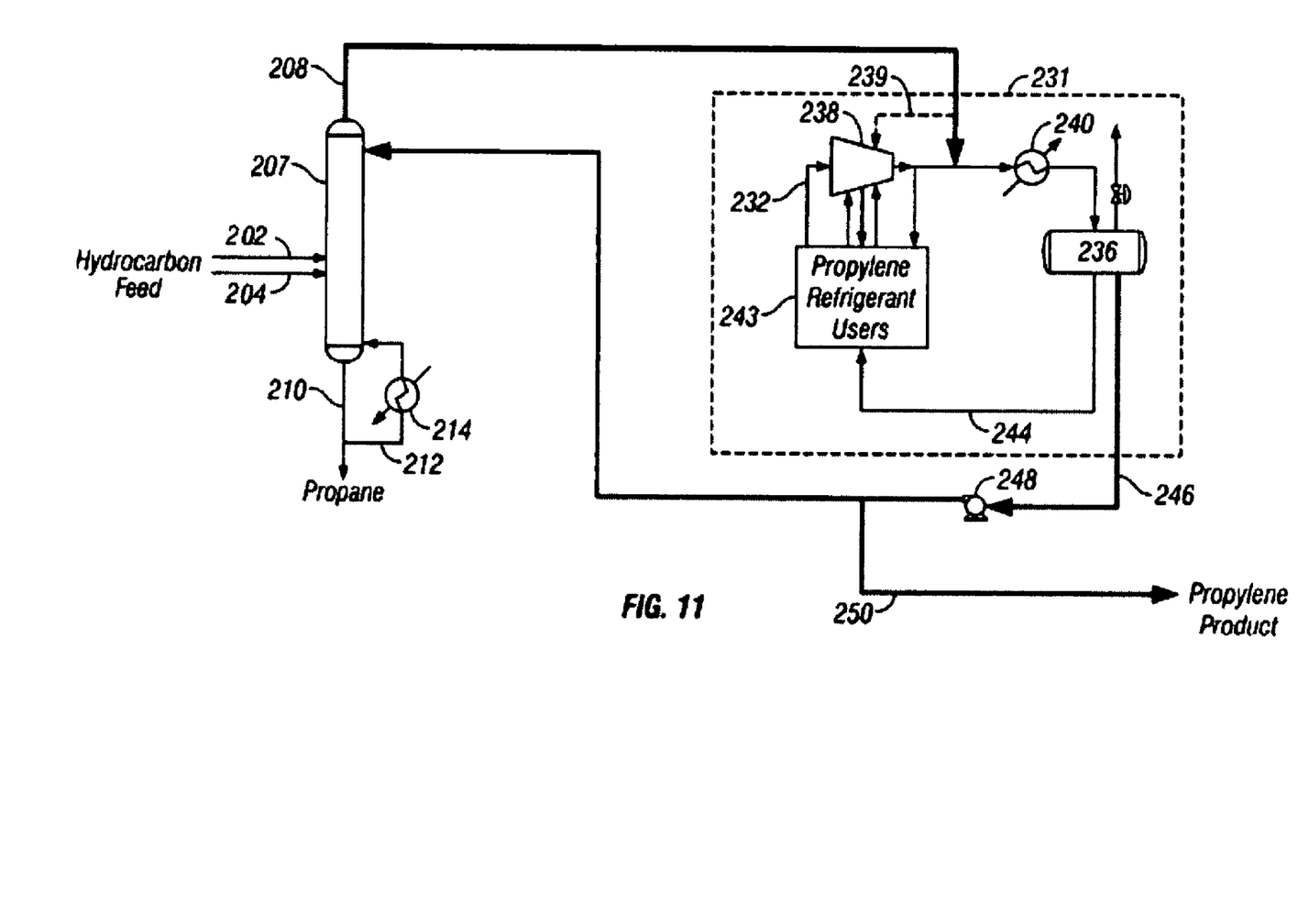
FIG. 11 depicts a schematic illustration of one embodiment, wherein a propane/propylene splitter is integrated with a propylene refrigeration unit, wherein the splitter overhead is supplied directly to the refrigeration unit, and wherein the splitter is refluxed with hot propylene from the refrigeration unit, in a propylene recovery process corresponding to FIG. 6a and FIG. 6b.

FIG. 11 depicts a schematic illustration of one embodiment, wherein a propane/propylene splitter is integrated with a propylene refrigeration unit, wherein the splitter overhead is supplied directly to the refrigeration unit, and wherein the splitter is refluxed with hot propylene from the refrigeration unit, in a propylene recovery process corresponding to FIG. 6a and FIG. 6b. This example process can include a C3 fractionation column 207, and a propylene refrigerant compressor train 231.

Hydrocarbon feeds 202 comprising propane and propylene is supplied via lines 204 to a propylene-propane splitter 207, which can produce an overhead stream 208 comprising primarily propylene and a bottoms stream 210 comprising primarily propane. The propylene overhead vapor 208 can be supplied from the propylene-propane splitter 207 to the refrigeration train 231. Depending on the pressure and temperature, the propylene vapor stream 208 can be fed to a stage in compressor 238 via line 239. The overhead vapor 208 can be condensed with condenser 240 and supplied to drum 236. The drum 236 can supply liquid propylene refrigerant to associated refrigerant consumers 243 via line 244. The associated propylene consumers 243 supply the propylene refrigerant to the compressor 238 of the refrigerant train via line 232. The splitter 207 can be refluxed with propylene from accumulator drum 236, supplied via line 246 and pump 248. Propylene product can be collected from line 246 via line 250. Integration of the propylene refrigerant train 231 to the propylene recovery process eliminates the need for the splitter condenser 216 and reflux drum 218 of the prior art process of FIG. 6a. To accommodate the increased volume of propylene to the refrigeration system 231, the refrigeration condenser 240 can be increased in capacity.

While these embodiments have been described with emphasis on the embodiments, it should be understood that within the scope of the appended claims, the embodiments might be practiced other than as specifically described herein.

What is claimed is:

1. A process for separating light hydrocarbons, comprising:
    introducing a light hydrocarbon comprising at least one alkane component and at least one olefin component to a fractionation column to obtain an overhead olefin vapor;
    introducing the overhead olefin vapor to a chiller/condenser of an olefin refrigeration compressor train at a location downstream of a compressor, wherein there is no intervening chiller/condenser located between the compressor and the chiller/condenser;
    chilling and condensing the overhead olefin vapor within the olefin refrigeration compressor train to obtain liquid olefin refrigerant;
    refluxing the fractionation column with a first portion of the liquid olefin refrigerant;
    introducing a second portion of the liquid olefin refrigerant to additional refrigerant consumers to produce at least one olefin refrigerant vapor;
    introducing the at least one olefin refrigerant vapor to the compressor; and
    recovering a third portion of the liquid olefin refrigerant as an olefin product.

2. The process of claim 1, wherein the light hydrocarbon comprises propane and propylene and the fractionation column is a propane-propylene splitter.

3. The process of claim 1, wherein the light hydrocarbon comprises ethane and ethylene, and the fractionation column comprises an advanced deethanizer with the first portion of the liquid olefin refrigerant refluxing a deethanizer column and an ethylene-ethane splitter.

4. The process of claim 3, further comprising heat pumping the ethylene-ethane splitter with ethylene from the olefin refrigeration compressor train.

5. An apparatus for separating light hydrocarbons, comprising:
    means for introducing a light hydrocarbon comprising at least one alkane component and at least one olefin component to a fractionation column to obtain an overhead olefin vapor;
    means for introducing the overhead olefin vapor to an olefin refrigeration compressor train at a location downstream of a compressor;
    means for supplying the overhead olefin vapor to a chiller/condenser located downstream of the compressor with no intervening chillers/condensers between the compressor and the chiller/condenser;

means for chilling and condensing the overhead olefin vapor within the olefin refrigeration compressor train to obtain liquid olefin refrigerant;

means for refluxing the fractionation column with a first portion of the liquid olefin refrigerant;

means for expanding and heating a second portion of the liquid olefin refrigerant to form at least one olefin refrigerant vapor stream for supply to the compressor; and means for recovering a third portion of the liquid olefin refrigerant as an olefin product.

6. The process of claim 1, wherein the olefin refrigeration compressor train condenses an overhead vapor from a second fractionation column.

7. The process of claim 1, further comprising refluxing a second fractionation column with a third portion of the liquid olefin refrigerant.

8. The process of claim 1, wherein the additional refrigerant consumers heat and expand the second portion of the liquid olefin refrigerant to produce a plurality of olefin refrigerant vapor streams, wherein the plurality of olefin refrigerant vapor streams are introduced to the compressor.

* * * * *